United States Patent
Wang et al.

(10) Patent No.: US 11,065,457 B2
(45) Date of Patent: Jul. 20, 2021

(54) METHOD FOR WAKING UP AN IMPLANTABLE MEDICAL DEVICE FROM A DORMANT STATE, IMPLANTABLE MEDICAL DEVICE, AND SYSTEM COMPRISING SUCH AN IMPLANTABLE MEDICAL DEVICE AND AN EXTERNAL DEVICE

(71) Applicant: BIOTRONIK SE & CO. KG, Berlin (DE)

(72) Inventors: Yu Wang, Lake Oswego, OR (US); Brian P. Sutton, West Linn, OR (US); Paul Stadnik, Lake Oswego, OR (US); David Kosokowsky, Lake Oswego, OR (US); Brad McMillan, Lake Oswego, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 158 days.

(21) Appl. No.: 16/280,231

(22) Filed: Feb. 20, 2019

(65) Prior Publication Data
US 2020/0261733 A1 Aug. 20, 2020

(51) Int. Cl.
*A61N 1/372* (2006.01)
*H04W 52/02* (2009.01)
*H04B 1/40* (2015.01)

(52) U.S. Cl.
CPC ..... *A61N 1/37276* (2013.01); *A61N 1/37217* (2013.01); *H04W 52/0274* (2013.01); *A61N 1/37235* (2013.01); *H04B 1/40* (2013.01)

(58) Field of Classification Search
CPC ............ A61N 1/37276; A61N 1/37217; A61N 1/37235; A61N 1/3727
(Continued)

(56) References Cited

U.S. PATENT DOCUMENTS 8,428,528 B2 4/2013 Sutton et al.
8,577,327 B2 11/2013 Makdissi et al.
(Continued)

FOREIGN PATENT DOCUMENTS

EP 2441491 A1 4/2012

OTHER PUBLICATIONS

Zgaren Mohamed et al: "Low-Power, High-Data Rate 915 MHz Transceiver with Fully Passive Wake-Up Receiver for Biomedical Implants", 2015 IEEE International Conference on Ubiquitous Wireless Broadband (ICUWB), IEEE, Oct. 4, 2015 (Oct. 4, 2015), pp. 1-4, XP032809372, DOI: 10.1109/ICUWB.2015.7324471 [retrieved on Nov. 10, 2015].

*Primary Examiner* — Amanda K Hulbert
*Assistant Examiner* — Philip C Edwards
(74) *Attorney, Agent, or Firm* — Laurence A. Greenberg; Werner H. Sterner; Ralph E. Locher

(57) ABSTRACT

A method for waking up an implantable medical device from a dormant state, an implantable medical device, and a system that includes such an implantable medical device and an external device. The implantable medical device is woken up from a dormant state by sending a modulated wakeup signal via a wireless link from an external device. The modulated wakeup signal is demodulated by way of a demodulator circuitry of the implantable medical device so as to produce a demodulated wakeup signal. The demodulator circuitry is permanently ready for operation. An awake state of the implantable medical device is then activated in response to the demodulated wakeup signal.

14 Claims, 4 Drawing Sheets

(58) Field of Classification Search
USPC .......................................................... 607/60
See application file for complete search history.

(56) References Cited

U.S. PATENT DOCUMENTS

| | | |
|---|---|---|
| 8,963,737 B2 | 2/2015 | Makdissi |
| 2012/0093245 A1* | 4/2012 | Makdissi ............. A61B 5/0028 375/259 |
| 2012/0215286 A1* | 8/2012 | Rahman ............. A61N 1/37288 607/60 |
| 2013/0090705 A1* | 4/2013 | Bange ................ A61N 1/37276 607/60 |
| 2015/0065047 A1 | 3/2015 | Wu et al. |

* cited by examiner

METHOD FOR WAKING UP AN IMPLANTABLE MEDICAL DEVICE FROM A DORMANT STATE, IMPLANTABLE MEDICAL DEVICE, AND SYSTEM COMPRISING SUCH AN IMPLANTABLE MEDICAL DEVICE AND AN EXTERNAL DEVICE

BACKGROUND OF THE INVENTION

Field of the Invention

The instant invention generally relates to a method for waking up an implantable medical device from a dormant state. The instant invention also relates to an implantable medical device as well as to a system comprising such an implantable medical device and an external device.

The function of an implantable medical device, such as e.g. an implantable pulse generator of a cardiac pacemaker, is usually constrained by battery life. Therefore, RF transceivers of implantable medical devices are typically kept in a dormant state over extended periods to conserve power. Any wireless communication session with an external device therefore requires a method of waking up the device's RF transceiver. In this context, it is generally desirable that an implant circuitry uses a minimal amount of power, especially if false alarms (i.e., unintended wakeup events) can be expected. Further, a reliable authentication is needed to ensure that the device is woken up only by the proper external device. As a result of a valid authentication, the implantable medical device will be woken up, i.e., put in a higher power consumption communications state.

Existing solutions for waking up an implantable medical device rely, for example, on an inductive coil communication, wherein an inductive wand is placed within a few centimeters of the device to wake it up. Such methods require the inductive wand to be placed in close proximity (about 2 cm) of the implantable medical device.

In another existing approach, the patient uses the static magnetic field of a magnet for initiating communication with an implanted medical device. This wakeup method has the inconvenience that it requires additional hardware and precludes any other magnet modes (e.g. a therapy or auto-MRI mode).

A further known solution is based on dedicated external RF hardware that generates a wakeup message (e.g. in the ISM band). However, the wakeup via custom-made external hardware requires the design, fabrication and distribution of the external hardware, which is generally costly. In such an approach, hardware support functions will also be required.

Yet another approach provides for a periodic wakeup of an RF receiver of an implantable medical device and a decoding of a wakeup message. For example, the US patent application 2015/0065047 A1 discloses turning an external communication device into an advertising device for an implantable medical device. The implantable medical device comprises an RF detector circuit. It is proposed to use the Bluetooth standard for communication between the implantable medical device and the external device (e.g. a smartphone). The implantable medical device regularly performs a scan sequence in which it searches for a Bluetooth advertising signal from the external device. If an advertising signal from the external device is detected, a communication connection between implantable medical device and external device is established. This solution may, for example, utilize the Bluetooth capability of a smartphone used as an external device. However, the implantable medical device needs to periodically perform an RF (e.g. Bluetooth) receiver sniffing in order to detect and decode the advertising message from the smartphone. As a result, this known wakeup method still consumes a relatively high amount of battery power. In addition, the wakeup may be relatively slow depending on the period between consecutive RF receiver sniffing sequences.

It is thus an object of the present invention to provide a method for waking up an implantable medical device from a dormant state which overcomes the above-mentioned inconveniences of known methods. For example, it is desirable to provide for a more power efficient wakeup procedure. Further, the wakeup process shall have little latency and shall thus be faster than known solutions. In addition, the method shall allow for a reliable authentication of an external device that is authorized for communication with the implantable medical device. Further, there is a desire for providing an implantable medical device and a system comprising such an implantable medical device and an external device which support such a method.

BRIEF SUMMARY OF THE INVENTION

According to a first aspect of the instant invention, a method for waking up an implantable medical device from a dormant state comprises at least the following steps: sending a modulated wakeup signal via a wireless link by means of an external device; demodulating the modulated wakeup signal by means of demodulator circuitry of the implantable medical device so as to produce a demodulated wakeup signal, wherein the demodulator circuitry is permanently ready for operation; and activating an awake state of the implantable medical device in response to the demodulated wakeup signal.

Hence, it is proposed to initiate a wakeup procedure by means of a modulated wakeup signal transmitted by the external device. The wakeup signal can then be immediately demodulated by means of the demodulator circuitry of the implantable medical device, wherein the demodulator circuitry is permanently ready for operation (always on). Advantageously, with this solution, the implantable medical device itself does not need to actively scan for a wakeup signal. Instead, the external device emits a modulated signal, which is detected by the demodulator passively. Due to the omission of scanning, a fast and low-energy wakeup process is achieved. In other words, the always-on demodulator circuitry eliminates the need for a periodical scan (such as a periodical RF sniff) of the implanted medical device, resulting in power saving and a shortened latency for the wakeup.

In an embodiment, the implantable medical device comprises a communications transceiver circuitry being configured to support a wireless communication with the external device in the awake state. For example, the wireless communication may use an RF link. The wireless communication may be carried out according to an established communication standard, such as, e.g., Bluetooth.

Further, the communications transceiver circuitry may be configured to assume a low-power-consumption mode in the dormant state of the implantable medical device. The communications transceiver circuitry may be inactive in the low-power-consumption mode. For example, a wireless communication between the communications transceiver circuitry of the implantable medical device and the external device may thus not be supported in the dormant state. Upon activating the awake state (and thereby exiting the dormant state), the implantable medical device may power up the communications transceiver for enabling a user communication, e.g., a telemetry session.

For example, the implantable medical device may comprise an antenna that is configured to receive the modulated wakeup signal sent by the external device. In an embodiment, the antenna is also configured to support the wireless communication (supported by the communications transceiver circuitry) with the external device in the awake state. In other words, a wakeup detection circuitry (comprising, in particular, the demodulator circuitry) and the communications transceiver circuitry may share the same antenna and potentially a portion of the signal path. This has the advantage that less components are required and production costs may thus be reduced. In particular, with such a solution, there is no need to provide additional RF switches.

In an embodiment, the implantable medical device comprises a frontend matching circuitry that is connected to each of the antenna and the demodulator circuitry. The frontend matching circuitry is configured to filter the modulated wakeup signal before it is transmitted to the demodulator circuitry. The frontend matching circuitry may be installed upstream to the demodulator circuitry. Hence, the modulated wakeup signal is first received by means of an antenna of the implantable medical device and then filtered by means of a frontend matching circuitry of the implantable medical device before being transmitted to the demodulator circuitry. For example, while the implantable medical device is in the dormant state, the frontend matching circuitry can make sure that incoming signals received by the antenna are transmitted to the demodulator circuitry (instead of being received by, e.g., a communications transceiver circuitry, such as a Bluetooth chip).

In an embodiment, the modulated wakeup signal is an amplitude modulated signal, such as, e.g., a signal modulated by means of amplitude shift keying (ASK). Correspondingly, in an embodiment, the demodulator circuitry may be an amplitude demodulator circuitry, such as an ASK demodulator circuitry. For example, in such an embodiment, a payload of the wakeup message may not be important and will not be decoded. Instead, an RF amplitude change in the time domain may be indicative of a valid wakeup request. This may be beneficial in terms of privacy protection, since no private information is used for wakeup and/or authentication.

Further, in an embodiment, the demodulator circuitry may be implemented as a zero-power-consumption demodulator circuitry, e.g., in the form of a zero-power-consumption RF envelope ASK demodulator. Employing such a zero-power-consumption ASK demodulator, which is permanently ready to receive, may eliminate the need to periodically turn on a receiver (such as a Bluetooth receiver) to decode potentially incoming advertising/wakeup packets. This may result in significant power saving for the implantable medical device.

For example, such an ASK demodulator circuitry may be implemented with an optimized envelope sensitivity to minimize false wakeup events. For example, a series inductor may be provided to accurately control an input impedance of the demodulator circuitry. Further, the ASK demodulator circuitry may be designed in such a way that it is capable of detecting a wakeup signal only in close proximity (e.g. up to several inches) to the external device from which the wakeup signal is transmitted. The required proximity and/or the optimized envelope sensitivity add to the security of the pairing between the external device and the implantable medical device.

In an embodiment, the implantable medical device further comprises a match detector circuitry that is configured to validate the demodulated wakeup signal (e.g., a baseband signal). For example, the match detector circuitry may be provided in the form of an ultra-low-power baseband detector circuitry, such as an ultra-low-power ASK match detector circuitry (in case the demodulator circuitry is an ASK demodulator circuitry). The ASK match detector circuitry is configured to receive the demodulated wakeup signal from the ASK demodulator circuitry, to verify the received wakeup signal and to initiate a wakeup, i.e., the activation of the awake state, of the implantable medical device based on said verification. For example, the match detector circuitry recognizes a valid wakeup signal according to its amplitude and frequency.

In an embodiment, the implantable medical device comprises control circuitry, such as a baseband controller, that is configured to activate the awake state in response to the demodulated wakeup signal. For example, said control circuitry and the match detector circuitry are integrated in a baseband controller. Further, in an embodiment, the demodulator module may also be integrated in a baseband controller, e.g., together with said control circuitry and/or the match detector circuitry. In another embodiment, the demodulator circuitry may be provided separately from a baseband controller, e.g., as a discrete circuit.

The external device may function, for example, as a so-called patient remote. Additionally, the external device may function as an authentication device. In an embodiment, the external device is a mobile device, such as a smartphone. For example, the method according to the instant invention allows for using a commercial smartphone as an external secure wakeup/authentication device. The wakeup method shall be secure but portable, such that only a smartphone with customized software can be used to wake up the implant (preferably only at close proximity). It is convenient for a patient to unite the functionality of a patient remote and an authentication device in one smartphone. This alleviates the need for a separate patient activator (e.g., a magnet or inductive coil), since most patients already carry a smartphone. The patient may thus use a commercial smartphone as a secure patient activator to wake up the implantable medical device. Once paired with an implant, additional smartphone features may be employed. As a result, since no customized hardware external to the implantable medical device is needed, the system costs may be reduced.

In an embodiment, the external device is capable of generating the modulated wakeup signal in the form of a specific RF wakeup sequence, which may be, for example, specified by the vendor of the implantable medical device. A software of the external device that controls the wakeup protocol may also be capable of switching the external device from an advertising mode into a scan/connect mode according to a specific sequence. In other words, a commercially available external device, such as a smartphone, may be provided with customized software that controls the wakeup advertising sequence and the role switching from advertise to scan/connect.

Further, in an embodiment, the wakeup protocol may be compatible with an established communication standard, such as the Bluetooth protocol. Thus, in accordance with a preferred embodiment, the wakeup protocol is not covered by but compatible with the Bluetooth standard. For example, specific Bluetooth compatible advertising and/or extended advertising transmission sequences may be created. In an exemplary embodiment, a BLE5.0 extended advertising sequence is used as a wakeup signal sequence. Hence, in accordance with some embodiments, the modulated wakeup signal may be transmitted via a Bluetooth interface of the external device.

In an embodiment, the method according to the present invention further comprises, after activating the awake state, activating an advertising mode of a communications transceiver circuitry of the implantable medical device. For example, software for the control circuitry of the implantable medical device may be configured to turn on a communications transceiver circuitry, such as a Bluetooth chipset, of the implantable medical device upon detection of a valid wakeup signal. The communications transceiver circuitry may subsequently start advertising so as to initiate a communication session with the external device, e.g., according to a handshake protocol required by the standard.

More generally, in an embodiment, the method may further comprise, after activating the awake state, establishing a communication session between the implantable medical device and the external device. For example, the communication session may be supported by respective communications transceiver circuitries (e.g., Bluetooth chip sets) of the implantable medical device and the external device.

According to a second aspect of the instant invention, an implantable medical device is configured to selectively assume an awake state and a dormant state and comprises: a communications transceiver circuitry being configured to support a wireless communication with an external device in the awake state, wherein the communications transceiver circuitry assumes a low-power-consumption mode in the dormant state; an antenna being configured to receive a modulated wakeup signal sent by the external device; a demodulator circuitry being configured to demodulate the modulated wakeup signal so as to produce a demodulated wakeup signal, wherein the demodulator circuitry is permanently ready for operation; and control circuitry being configured to activate the awake state in response to the demodulated wakeup signal.

According to a third aspect of the instant invention, a system comprises an implantable medical device according to the first aspect of the invention and an external device being configured to send a modulated wakeup signal via a wireless link so as to wake up the implantable medical device. For example, the external device may also be configured to generate the modulated wakeup signal by means of customized software.

The implantable medical device according to the second aspect of the present invention and the system according to the third aspect of the present invention may be used for carrying out the method of the first aspect of the present invention. In other words, the components of the implantable medical device according to the second aspect and of the system according to the third aspect may be configured for carrying out corresponding method steps. For example, the implantable medical device of the second or third aspect may correspond to the implantable medical device referred to in connection with the method according to the first aspect. Likewise, the external device of the system according to the third aspect may correspond to the external device referred to in connection with the method according to the first aspect. Correspondingly, what has been described above and will be described in the following with reference to the method of the first aspect, may analogously apply to the implantable medical device and the system according to the second and third aspects, and vice versa.

Although the invention is illustrated and described herein as embodied in a displacement aid for desktop devices cross-reference to related application, it is nevertheless not intended to be limited to the details shown, since various modifications and structural changes may be made therein without departing from the spirit of the invention and within the scope and range of equivalents of the claims.

BRIEF DESCRIPTION OF THE SEVERAL VIEWS OF THE DRAWING

The various features and advantages of the present invention may be more readily understood with reference to the following detailed description and the exemplary embodiments shown in the drawings.

DETAILED DESCRIPTION OF THE INVENTION

Figure 1:
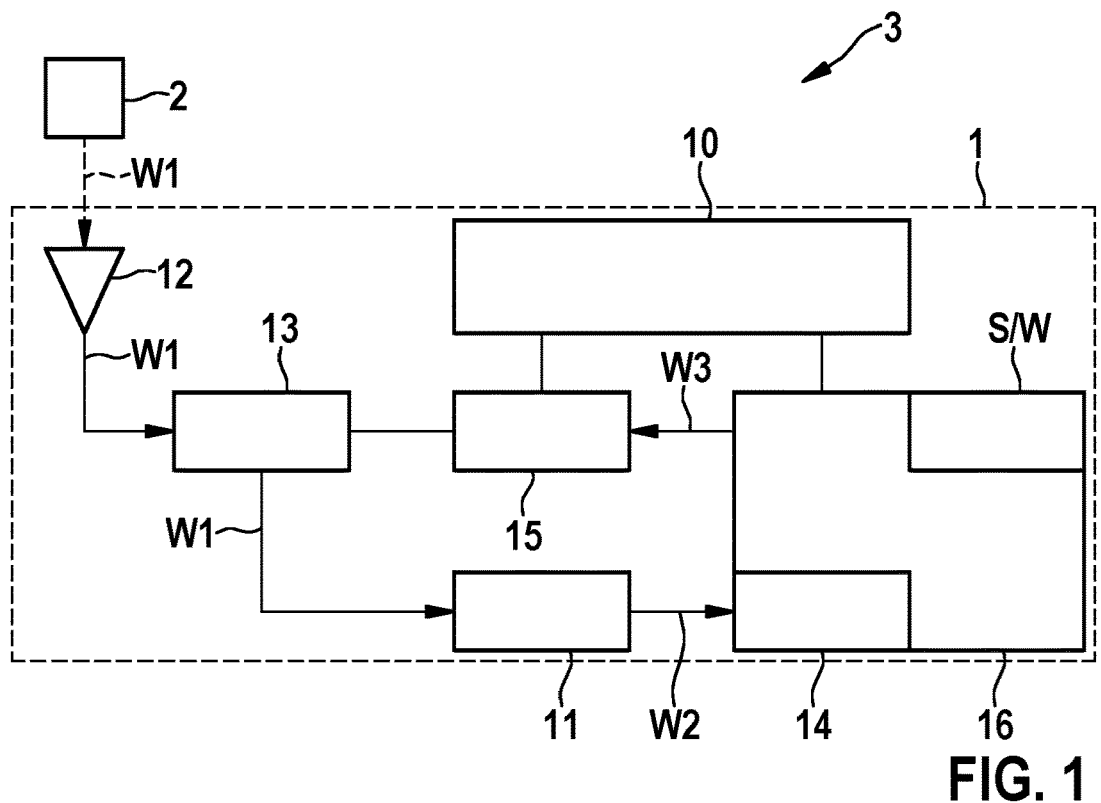
FIG. 1 shows a schematic view of a system comprising an implantable medical device and an external device.

In the following, embodiments of the invention shall be described in detail with reference to the drawings. In the drawings, like reference numerals designate like structural elements.

It is to be noted that the embodiments are not limiting for the invention, but merely represent illustrative examples.

FIG. 1 shows a schematic view of a system 3 comprising an implantable medical device 1 and an external device 2. In the present exemplary embodiment, the external device 2 is a smartphone that is used by a patient as a patient remote. The implantable medical device 1 may be or may comprise, for example, a pulse generator of a cardiac pacemaker that is implanted in the patient's body. In FIG. 1, only a communications module of the implantable medical device 1 is depicted. Further components of the implantable medical device 1, such as, e.g., a memory, a therapy delivery unit, or other components, are not shown in FIG. 1 for simplicity.

The implantable medical device 1 comprises a communications transceiver circuitry 15, e.g. in the form of a Bluetooth chip, which is configured to support a wireless communication with the external device 2. Further, the implantable medical device 1 comprises a control circuitry 16, e.g. in the form of a baseband controller, which is connected to the communications transceiver circuitry 15. Both the communications transceiver circuitry 15 and the control circuitry 16 are connected to a power supply 10 of the implantable medical device 1.

The implantable medical device 1 is configured to selectively assume an awake state and a dormant state. In the awake state, the communications transceiver circuitry 15 is active so as to support the wireless communication with the external device 2. In the dormant state, the communications transceiver circuitry 15 (i.e., both transmitter and receiver)

assumes a low-power-consumption mode, which does not support the wireless communication with the external device 2.

The external device 2 is configured to generate and send a modulated wakeup signal W1 via a wireless link (such as a Bluetooth link) so as to wake up the implantable medical device 1, i.e., trigger a transition of the implantable medical device 1 from its dormant state to its awake state. For example, to this end, the external device 2 comprises customized software that supports the generation of the modulated wakeup signal W1. The modulated wakeup signal W1 may be compatible with the Bluetooth standard. For example, the modulated wakeup signal W1 may take the form of a customized advertising sequence compatible with BLE5.0. In the present embodiment, the modulated wakeup signal W1 is an amplitude shift keying (ASK) signal.

The modulated wakeup signal W1 is received by an antenna 12 of the implantable medical device 1. The antenna 12 is connected to the communications transceiver circuitry 15 via a frontend matching circuitry 13. Thus, the antenna 12 is arranged and configured to support the wireless user communication with the external device 2 in the active state of the implantable medical device 1.

The frontend matching circuitry 13 is also connected to a demodulator circuitry 11, wherein the frontend matching circuitry 13 is installed upstream to the demodulator circuitry 11, i.e., between the antenna 12 and the demodulator circuitry 11. The frontend matching circuitry 13 is configured to receive and filter the modulated wakeup signal W1 before transmitting it to the demodulator circuitry 11. While the implantable medical device 1 is in the dormant state, the frontend matching circuitry 13 makes sure that an incoming modulated wakeup signal W1 is transmitted to the demodulator circuitry 11 instead of being transmitted to the communications transceiver circuitry 15.

Figure 2:
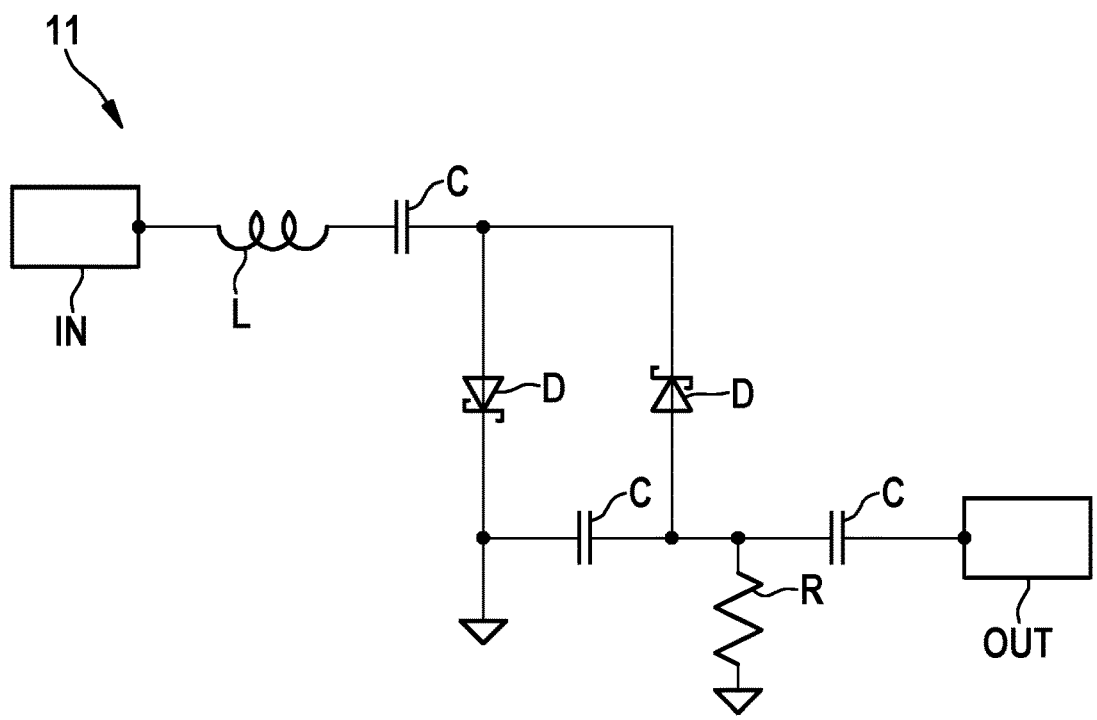
FIG. 2 schematically illustrates a demodulator circuitry.

In the present exemplary embodiment, the demodulator circuitry 11 is a zero-power-consumption ASK demodulator circuitry that is permanently ready to operate. An example of such an always-on, zero-power-consumption ASK demodulator 11 is illustrated in FIG. 2, which will be described in more detail further below.

The always-on ASK demodulator circuitry 11 is configured to demodulate the modulated wakeup signal W1 so as to generate a demodulated wakeup signal W2 (e.g., a baseband signal). For example, to this end, the ASK demodulator circuitry 11 is configured to extract an envelope of the modulated wakeup signal W1 so as to produce the demodulated wakeup signal W2.

The demodulated wakeup signal W2 is subsequently transmitted to a match detector circuitry 14 that is configured to validate the demodulated wakeup signal W2. This is to say that the match detector circuitry 14 verifies the demodulated wakeup signal W2, wherein a valid wakeup signal W2 may be recognized according to its amplitude and frequency, for example. Hence, the match detector circuitry 14 may authenticate the external device 2 by verifying a valid wakeup signal W2.

The match detector circuitry 14 may be designed as an ultra-low-power baseband detector circuitry. In the present embodiment, the match detector circuitry 14 forms a part of the control circuitry 16 of the implantable medical device 1. In other embodiments, the match detector circuitry 14 may be separate from the control circuitry 16.

The control circuitry 16 may comprise software S/W stored in one or more memory units (not illustrated) as well as one or more processor units, which are controlled by the software S/W. The control circuitry 16 activates the awake state in response to the detection of a valid wakeup signal W2 by means of the match detector circuitry 14. For example, to this end, the control circuitry 16 may transmit a logical wakeup signal W3 to the communications transceiver circuitry 15. In response to the logical wakeup signal W3, the communications transceiver circuitry 15 may be powered up so as to be able to support the wireless user communication with the external device 2. For example, after activating the awake state, a wireless communication session, such as a telemetry session, between the implantable medical device 1 and the external device 2 may be established.

FIG. 2 schematically illustrates a demodulator circuitry 11, which may be employed, for example, in the implantable medical device 11 of FIG. 1. The depicted layout, which comprises a number of diodes D and capacitors C as well as a resistance R and an inductance L, realizes a zero-power-consumption always on ASK demodulator 11. The illustrated ASK demodulator circuitry 11 provides an optimized envelope sensitivity to minimize false wakeup events. In particular, the series inductor L is provided to accurately control an input impedance of the ASK demodulator circuitry 11. For example, by means of the series inductor L, an appropriate trade-off between the demodulator circuitry 11 and the main RF path in FIG. 1 (i.e., the path to the communications transceiver circuitry 15) may be adjusted. The DC blocking cap at the output of the demodulator circuitry 11 shown in FIG. 2 is provided for enabling an interface with existing Mesquite/Maple based RF wakeup IP blocks, which can be modified into two stage multi rate FIR filters for the match detection.

According to an embodiment of the present invention, the DC blocking cap allows the ASK waveform to be detected by the IP block that were implemented based on U.S. Pat. No. 8,428,528 B2 (See for example the baseband filtering and amplification unit 308 in FIG. 3 of said reference).

An ASK demodulator circuitry 11 such as the one that is exemplarily shown in FIG. 2 may be provided as a discrete circuitry or as an integrated circuit (e.g., based on the CMOS semiconductor fabrication technology). For example, in the latter case, the demodulator circuitry 11 may be integrated into the baseband controller 16. In that case, the baseband controller 16 must exhibit an analog input port capable of receiving an RF signal.

Figure 3:
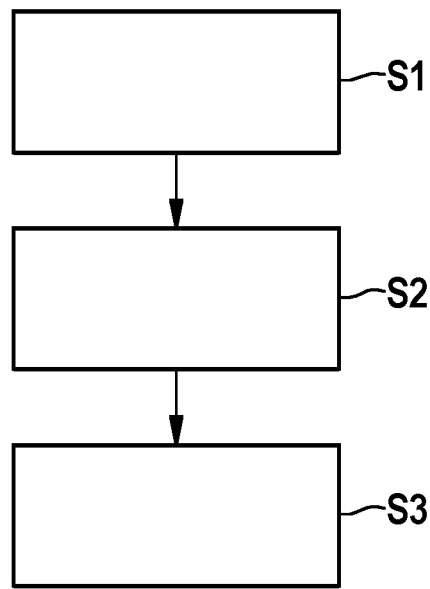
FIG. 3 is a schematic representation of the method according to the instant invention in the form of a block diagram.

FIG. 3 illustrates the method according to the instant invention in the form of a schematic block diagram. In a first step S1, the modulated wakeup signal W1 is transmitted by the external device 2 via the wireless link (e.g., Bluetooth). In a second step S2, the modulated wakeup signal W1 is demodulated and a demodulated wakeup signal W2 is thus generated by means of the zero-power-consumption always on ASK demodulator circuitry 11. In a third step S3, the awake state of the implantable medical device 1 is activated in response to the demodulated wakeup signal W2. Further details and intermediate steps in accordance with one or more embodiments have been addressed above and will be addressed in the following.

Figure 4:
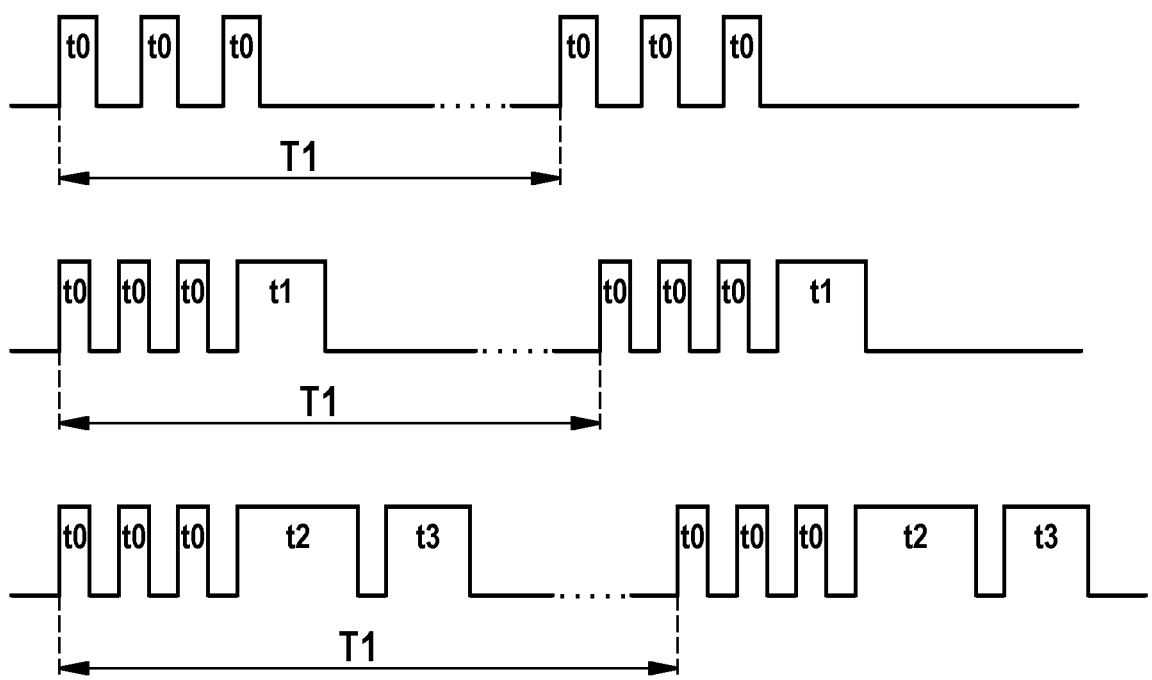
FIG. 4 schematically illustrates possible RF wakeup sequences for BLE devices.

FIG. 4 schematically illustrates possible RF wakeup sequences for Bluetooth Low Energy (e.g. BLE5) devices. Such wakeup sequences may be generated by the external device 2 by means of appropriate software. For example, the wakeup sequences may be generated in the form of customized (vendor-specific) Bluetooth advertising sequences. As illustrated, such signal sequences are characterized essentially by a period T1 and by one or more pulse durations t0, t1, t2, t3. These parameters T1, t0, t1, t2, t3 may be controlled at least to a certain degree by means of software, which may be provided by the vendor. It should be noted that the exemplary wakeup sequences shown in FIG. 4 yet have to be ASK modulated to form the modulated wakeup signal W1. In other words, the illustrated signal sequences may correspond to envelopes of the modulated wakeup signal W1, which may be reconstructed at the receiving end by means of the demodulator circuitry 11 of the implantable medical device 1.

In principle, the wakeup transmitter according to the invention can use ASK, FSK or any other modulation as desired. In the case of BLE protocol, the actual RF wakeup sequence generated is GFSK modulated packets sequence hopping over multiple BLE RF channels.

The 'always on' ASK detector of the implant according to embodiments of the present invention detects and translates the RF wakeup waveform to baseband ASK waveform. It then feed to the baseband detector in order to find a match and trigger the wakeup of the main BLE transceiver.

Figure 5:
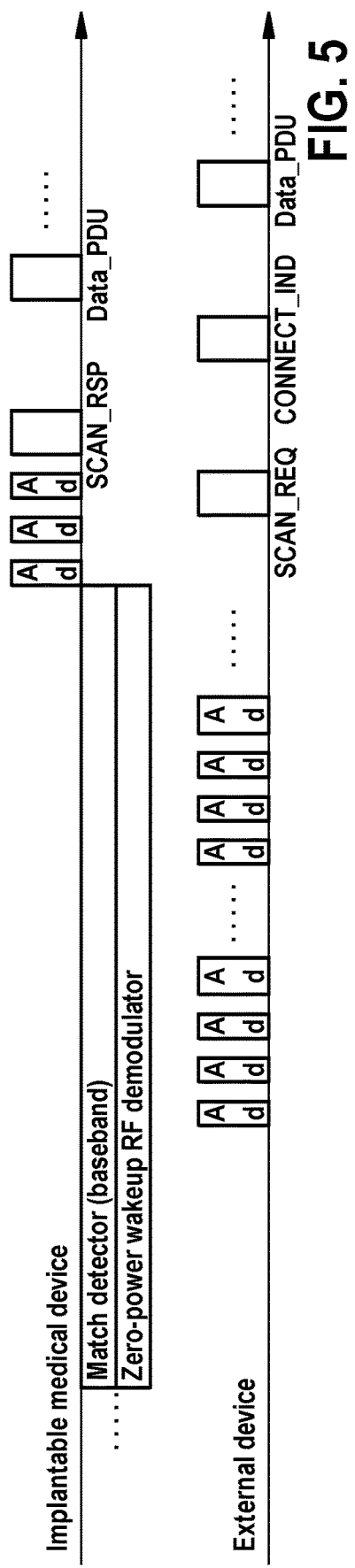
FIG. 5 schematically illustrates an exemplary wakeup protocol in accordance with one or more embodiments.

FIG. 5 schematically illustrates an exemplary wakeup protocol in accordance with an embodiment. In this example, the wakeup protocol is based on a BLE5.0 extended advertising sequence that is used as the wakeup sequence.

Initially, the implantable medical device 1 is in the dormant state, wherein the communications transceiver circuitry 15 is inactive and only the demodulator circuitry ("zero-power wakeup RF demodulator") and the match detector circuitry 11 ("Match detector (baseband)") are ready to operate.

Then, a communications transceiver of the external device 2 initiates a communication session, such as a telemetry session, with the implantable medical device 1. To this end, the external device 2 transmits an ASK modulated wakeup signal W1 that corresponds to a (customized) BLE5.0 extended advertising sequence. Such advertisement events are designated with the reference "Ad" in FIG. 5. Thus, in the present embodiment, a BLE portion of the wakeup protocol is driven by the external device 2.

The modulated wakeup signal W1 is received and processed by the implantable medical device 1 according to the procedure as described above with reference to FIGS. 1-4. As a result, the implantable medical device 1 activates its awake state.

After the activation of the awake mode, an advertising mode of the communications transceiver circuitry 15 of the implantable medical device 1 is activated (see reference "Ad" in the upper panel of FIG. 5). The external device 2 scans for an advertising package from the implantable medical device 1. Having received such an advertising package, the external device 2 sends a scan request ("SCAN_REQ") to the implantable medical device 1. Subsequently, in a connection/service discovery phase, further messages ("SCAN_RSP", "CONNECT_IND", "DATA_PDU") are exchanged between the external device 2 and the implantable medical device 1 so as to perform the necessary handshake according to the standard.

Figure 6:
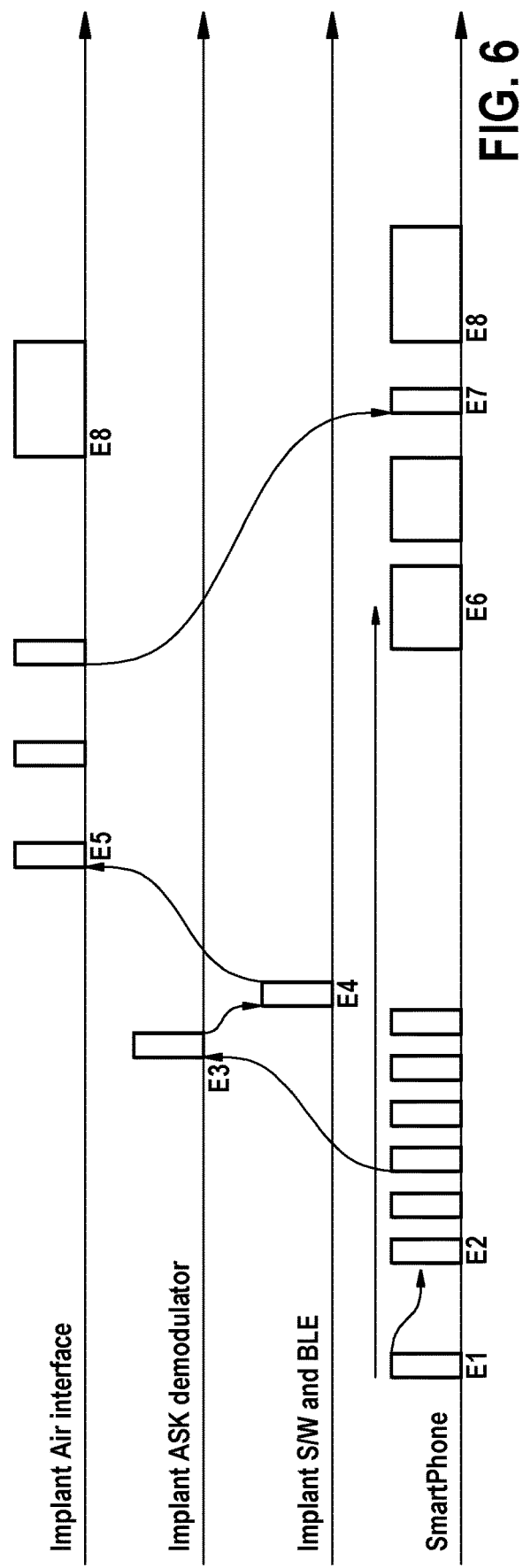
FIG. 6 schematically illustrates important events during a wakeup procedure in accordance with one or more embodiments.

FIG. 6 schematically and exemplarily illustrates important events E1-E8 that occur during a wakeup procedure in accordance with the embodiment described above with reference to FIG. 5: In the beginning, the external device 2 ("SmartPhone") starts a wakeup request event E1. Then, the external device 2 starts sending an advertising message in the form of an ASK modulated wakeup signal W1, wherein no private information is sent with the advertising message (event E2). In the subsequent event E3, the demodulator circuitry 11 of the implantable medical device 1 ("Implant ASK demodulator") demodulates the RF amplitude of the modulated signal W1 and passes the amplitude waveform (i.e., the demodulated wakeup signal W2) to the match detector circuitry 14 ("Implant S/W and BLE"). The match detector circuitry 14 then confirms that a valid wakeup sequence has been received, thereby authenticating the external device 2 (event E4). Next, the Bluetooth communications transceiver circuitry 15 ("Implant Air interface") of the implantable medical device 1 is set into an advertising mode (event E5). The external device 2 transitions to a scan mode after a programmable time as measured from the wakeup request (event E6). Having received an advertising package sent by the implantable medical device 1, the external device 2 sends a scan request to the implantable medical device 1 (event E7). Subsequently, the external device 2 and the implantable medical device 1 enter into a connection/service discovery phase and perform the necessary handshake according to the standard (event E8).

It should be noted that in this exemplary embodiment of a wakeup procedure, the implantable medical device 1 never enters into a scan mode.

Figure 7:
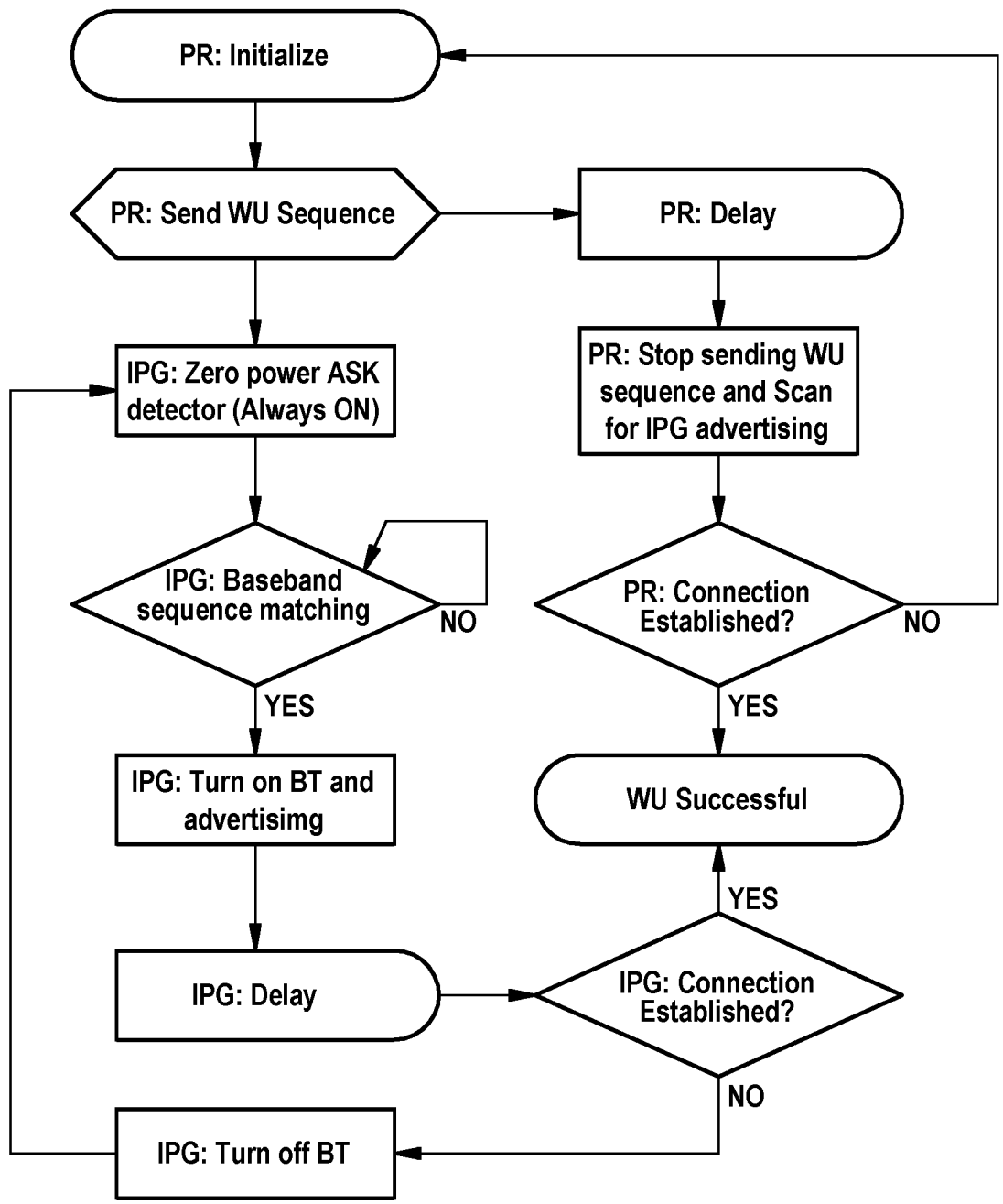
FIG. 7 shows a flow chart of a wakeup protocol in accordance with one or more embodiments.

FIG. 7 shows a flow chart of a wakeup (WU) protocol in accordance with, e.g., the embodiment described above with reference to FIGS. 5 and 6. In this exemplary embodiment, the external device 2 is referred to as a patient remote (PR), whereas the implantable medical device 1 is referred to as an implantable pulse generator (IPG).

The patient remote PR initializes the wakeup procedure and sends a wakeup sequence in the form of an ASK modulated wakeup signal W1. After a programmable delay, the patient remote PR stops sending the wakeup sequence and starts scanning for an advertising message from the implantable pulse generator IPG.

In the meantime, the wakeup sequence is received and demodulated by the always on ASK demodulator circuitry 11 ("Zero power ASK detector (Always ON)") of the implantable pulse generator IPG. A demodulated wakeup signal W2 is transferred from the demodulator circuitry 11 to the match detector circuitry 14 of the implantable generator IPG for verification ("Baseband sequence matching"). In case of a successful verification, the awake state of the implantable pulse generator IPG is activated. The Bluetooth communications transceiver circuitry 15 of the implantable pulse director IPG is then turned on and starts advertising by transmitting advertising messages. Such an advertising message may be received by the patient remote PR, which is in scan mode.

If the implantable pulse generator IPG determines after a programmable delay that a connection with the patient remote PR has been established, it considers the wakeup successful. In the alternative, if the implantable pulse director IPG determines that no connection has been established within the programmable delay period, the Bluetooth communications transceiver circuitry 15 is turned off again until the ASK demodulator circuitry 11 receives the next valid modulated wakeup signal W1.

Likewise, if the patient remote PR determines that a connection with the implantable pulse generator IPG has been established, it considers the wakeup successful. In the alternative, the patient remote PR initializes the wakeup procedure once again and the wakeup procedure starts from the beginning.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein.

Therefore, it is the intent to cover all such modifications and alternate embodiments as may come within the true scope of this invention.

LIST OF REFERENCE SIGNS

1 Implantable medical device
10 Power supply
11 Demodulator circuitry
12 Antenna
13 Frontend matching circuitry
14 Match detector circuitry
15 Communications transceiver circuitry
16 Control circuitry
2 External device
3 System
D Diode
E1-E8 Events
L Inductor
R Resistor
S1, S2, S3 Method steps
S/W Software
t0, t1, t2, t3 Pulse durations
T1 Period
W1 Modulated wakeup signal
W2 Demodulated wakeup signal
W3 Logical wakeup signal

The invention claimed is:

1. A method for waking up an implantable medical device from a dormant state, the method comprising:
sending a modulated wakeup signal via a wireless link from an external device;
demodulating the modulated wakeup signal by a demodulator circuitry of the implantable medical device so as to produce a demodulated wakeup signal, wherein the demodulator circuitry is permanently ready for operation, and the demodulator circuitry is a zero-power-consumption, amplitude shift keying demodulator circuitry; and
activating an awake state of the implantable medical device in response to the demodulated wakeup signal.

2. The method according to claim 1, wherein the demodulator circuitry is a zero-power-consumption demodulator circuitry.

3. The method according to claim 1, wherein the modulated wakeup signal is an amplitude modulated signal.

4. The method according to claim 1, which comprises sending the modulated wakeup signal via a Bluetooth interface of the external device.

5. The method according to claim 1, which comprises filtering the modulated wakeup signal by way of a frontend matching circuitry of the implantable medical device before being transmitted to the demodulator circuitry.

6. The method according to claim 1, which comprises validating the demodulated wakeup signal by way of a match detector circuitry of the implantable medical device prior to activating the awake state.

7. The method according to claim 1, further comprising, after activating the awake state, activating an advertising mode of a communications transceiver circuitry of the implantable medical device.

8. The method according to claim 1, further comprising, after activating the awake state, establishing a communication session between the implantable medical device and the external device.

9. An implantable medical device that is configured to selectively assume an awake state and a dormant state, the device comprising:
a communications transceiver circuitry configured to support a wireless communication with an external device in the awake state, and configured to assume a low-power-consumption mode in the dormant state;
an antenna configured to receive a modulated wakeup signal sent by the external device;
a demodulator circuitry configured to demodulate the modulated wakeup signal so as to produce a demodulated wakeup signal, said demodulator circuitry being permanently ready for operation, said demodulator circuitry being a zero-power-consumption, amplitude shift keying demodulator circuitry; and
a control circuitry configured to activate the awake state in response to the demodulated wakeup signal.

10. The implantable medical device according to claim 9, further comprising a frontend matching circuitry connected to said antenna and to said demodulator circuitry, said frontend matching circuitry being configured to filter the modulated wakeup signal prior to being transmitted to said demodulator circuitry.

11. The implantable medical device according to claim 9, further comprising a match detector circuitry configured to validate the demodulated wakeup signal.

12. The implantable medical device according to claim 9, wherein said antenna is configured to support the wireless communication with the external device in the awake state.

13. A system, comprising:
an implantable medical device according to claim 9; and
an external device configured to send a modulated wakeup signal via a wireless link in order to wake up the implantable medical device from the dormant state.

14. An implantable medical device that is configured to selectively assume an awake state and a dormant state, the device comprising:
a communications transceiver circuitry configured to support a wireless communication with an external device in the awake state, and configured to assume a low-power-consumption mode in the dormant state;
an antenna configured to receive a modulated wakeup signal sent by the external device;
a demodulator circuitry configured to demodulate the modulated wakeup signal so as to produce a demodulated wakeup signal, said demodulator circuitry being permanently ready for operation;
a control circuitry configured to activate the awake state in response to the demodulated wakeup signal; and
a frontend matching circuitry connected to said antenna and to said demodulator circuitry, said frontend matching circuitry being configured to filter the modulated wakeup signal prior to being transmitted to said demodulator circuitry.

* * * * *